United States Patent
Benizri-Carl et al.

[11] Patent Number: 5,798,525
[45] Date of Patent: Aug. 25, 1998

[54] X-RAY ENHANCED SEM CRITICAL DIMENSION MEASUREMENT

[75] Inventors: Peter Benizri-Carl, Alzey; Wolfgang Egert, Bodenheim; Manfred Jung, Limburg, all of Germany; Theodore Gerard van Kessel, Millbrook, N.Y.

[73] Assignee: International Business Machines Corporation, Armonk, N.Y.

[21] Appl. No.: 670,484

[22] Filed: Jun. 26, 1996

[51] Int. Cl.$^6$ ............................................. H01J 37/252
[52] U.S. Cl. ............................................. 250/310; 250/307
[58] Field of Search ............................... 250/310, 307, 250/306

[56] References Cited

U.S. PATENT DOCUMENTS

| | | | |
|---|---|---|---|
| 4,037,101 | 7/1977 | Okumura et al. | 250/310 |
| 4,467,199 | 8/1984 | Sato | 250/310 |
| 4,476,386 | 10/1984 | Reid et al. | 250/310 |
| 4,894,541 | 1/1990 | Ono | 250/310 |
| 4,988,872 | 1/1991 | Nagatsuka et al. | 250/310 |
| 5,414,265 | 5/1995 | Sartore | 250/310 |
| 5,481,109 | 1/1996 | Ninomiya et al. | 250/310 |

*Primary Examiner*—Kiet T. Nguyen
*Attorney, Agent, or Firm*—Whitham, Curtis, Whitham & McGinn; Stephen C. Kaufman

[57] ABSTRACT

Structures having high height to width ratios may be measured using X-ray techniques, where the surrounding base and the structure are composed of different substances. The technique combines X-ray detection with scanning electron microscope (SEM) beam scanning. The X-ray emission is set to detect the presence of a specific substance which is either in the structure or surrounding the structure.

6 Claims, 4 Drawing Sheets

NICKEL IRON SPECTRUM
NOTE Ni PEAK AT 0.85 KeV
APPROX. 1100 COUNTS/SEC

TOP SURFACE RESIST SPECTRUM
NOTE SUPPRESSION OF Ni PEAK
TO APPROX. 32 COUNTS/SEC

X-RAY ENHANCED SEM CRITICAL DIMENSION MEASUREMENT

DESCRIPTION

Background of the Invention

1. Field of the Invention

The present invention generally relates to semiconductor manufacture and, more particularly, to measurement of small scale devices.

2. Background Description

The manufacture of small scale devices (particularly those with sub-micron dimensions) including semiconductor devices, micro machined devices and thin film disk heads frequently requires the measurement of the lateral dimension of structures. In most cases this measurement in performed using optical microscopes (OM), scanning electron microscopes (SEM) and, more recently, atomic force microscopes (AFM).

There are two types of structures for which lateral dimension measurement is difficult or in some cases impossible for the standard measurement tools. Specifically, these are width measurement of the base of line structures and of trench structures where a material transition is involved. These two cases are illustrated in FIGS. 1A and 1B, respectively.

In FIG. 1A there is shown a cross section of a substrate 1 coated with a resist 2, having a trench 3. In FIG. 1B, there is a substrate 11 on which a pillar 12 has been formed. In FIG. 1A, the structure to be measured is the width of the base of the trench 3. In FIG. 1B, the structure to be measured is the base of pillar 12, next to substrate 11. In both cases the distance to be measured is smaller than the height of the structure; i.e., the depth of the trench 3 or the height of the pillar 12.

Precise lateral dimension measurement of these types of structures becomes progressively more difficult as the aspect ratio (ratio of the height to the width) becomes high and the lateral dimension approaches or falls below the micron scale in size. In each case, conventional measurement techniques begin to fail. Optical techniques are limited due to wavelength and numerical aperture limitation. SEM techniques are limited due to the dispersion of secondary electrons and AFM techniques are limited due to the probe dimensions. The conventional techniques mentioned above also lack significant material sensitivity (contrast). As an example, a trench in the region of concern consists of a rectangular slot 8 microns high and from 2 to 5 microns wide with resist sidewalls and NiFe seed layer at the base.

Conventional SEM measurements depend on the collection of secondary electrons to generate the signal for measurement. This frequently lacks the necessary contrast for good measurement and is sensitive to variation of sidewall angles. Typical SEM measurements on photo resist are performed below 1.0 Kev at low beam currents to avoid charging a damaging the photoresist. Measurement times on the order of seconds are now typical. A practical solution must be within these constraints.

SUMMARY OF THE INVENTION

It is therefore an object of the present invention to provide a signal for measurement of the base region dimensions of a trench structure. The inventive technique combines significant material sensitivity, low numerical aperture, high resolution and high throughput potential for lateral dimension measurement of the structure described above.

If the flourescent X-rays coming from the 0.85 Kev Ni L-alpha peak can be detected, it is possible to have a measurement signal that is not sensitive to the sidewall slope and that is exclusively selective of the bottom region of the trench. Further, if the primary SEM beam is set to an energy level just slightly above the Ni peak, significant contrast enhancement of the signal can be achieved. This contrast enhancement derives from the fact that electrons in the primary beam that collide with the photo resist would be down-scattered in energy below the Ni peak energy and thus incapable of generating florescent X-rays. Thus, only those primary electrons that collide directly with the NiFe seed layer could contribute to the X-ray signal.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF A PREFERRED EMBODIMENT OF THE INVENTION

The method according to the invention measures the lateral dimension of a structure that involves a material transition that takes advantage of the X-ray florescence characteristics of the different materials to achieve contrast using a standard scanning electron microscope (SEM) and an X-ray detection system. In most cases, the X-ray detection system will be of the energy dispersive type; however, it is not restricted as such in all cases.

Figure 1A:
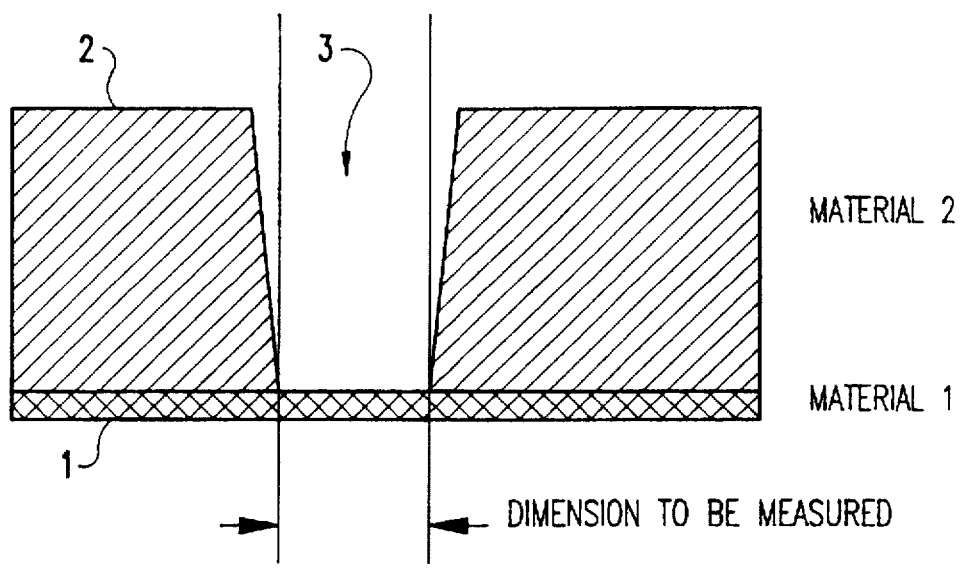
FIG. 1A is a cross-section showing a trench which is to be measured.
Figure 1B:
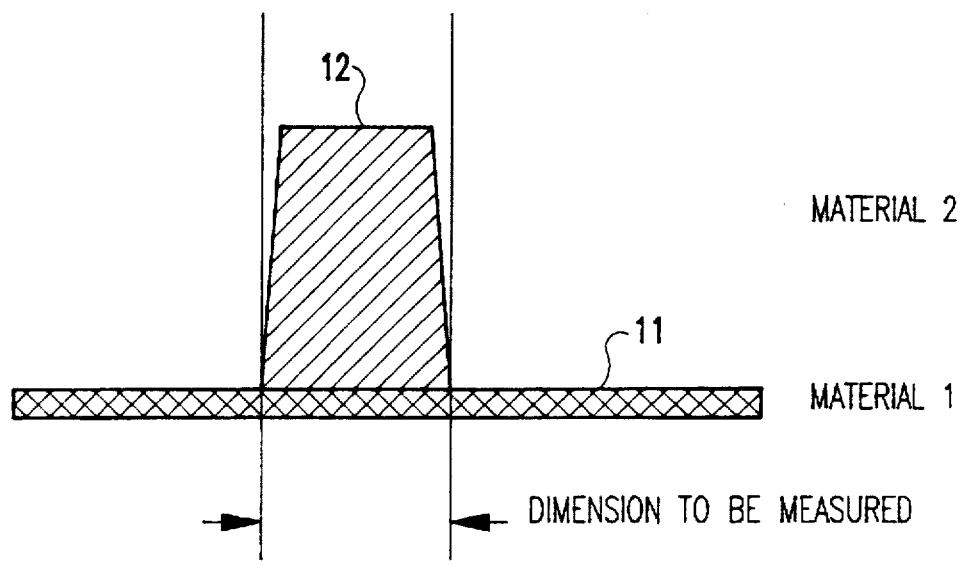
FIG. 1B is a cross-section showing a pillar structure in which the base is to be measured.
Figure 2A:
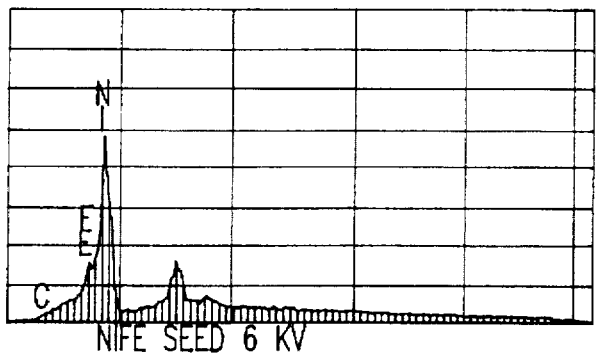
FIG. 2A is a graph showing the NiFe spectrum.
Figure 2B:
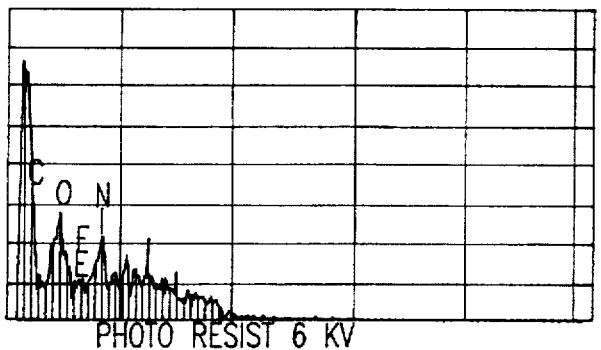
FIG. 2B is a graph showing the spectrum of a resist surface.

The method is carried out as follows:

The primary SEM beam energy is set at or above the energy of an X-ray flourescent peak that is characteristic of one of the material defining the feature of interest. This peak can be chosen for the material of the feature or that of the material defining the feature. For example, in the case of the write pole tip structure of the thin film disk head which consists of a trench in photo resist on top of a nickel-iron seed layer, one could choose either the nickel L-alpha peak or the seed layer or the carbon peak of the photo-resist. The X-ray peak is usually chosen such that it is distinct relative to other materials in the structure. FIG. 2 shows the X-ray flourescent spectra for the photo resist and nickel-iron material used in the write pole tip example above. As can be seen in FIG. 2B, the photo-resist will register peaks from several structures, including peaks which may represent structures in the target feature. FIG. 2A is simply the spectra of Nickel alone. If the target feature contains Nickel while the remainder of the substrate does not, the electron beam could be set at an energy slighty above the expected X-ray flourescence for Nickel. An X-ray will be generated when the target feature is scanned.

Figure 3:
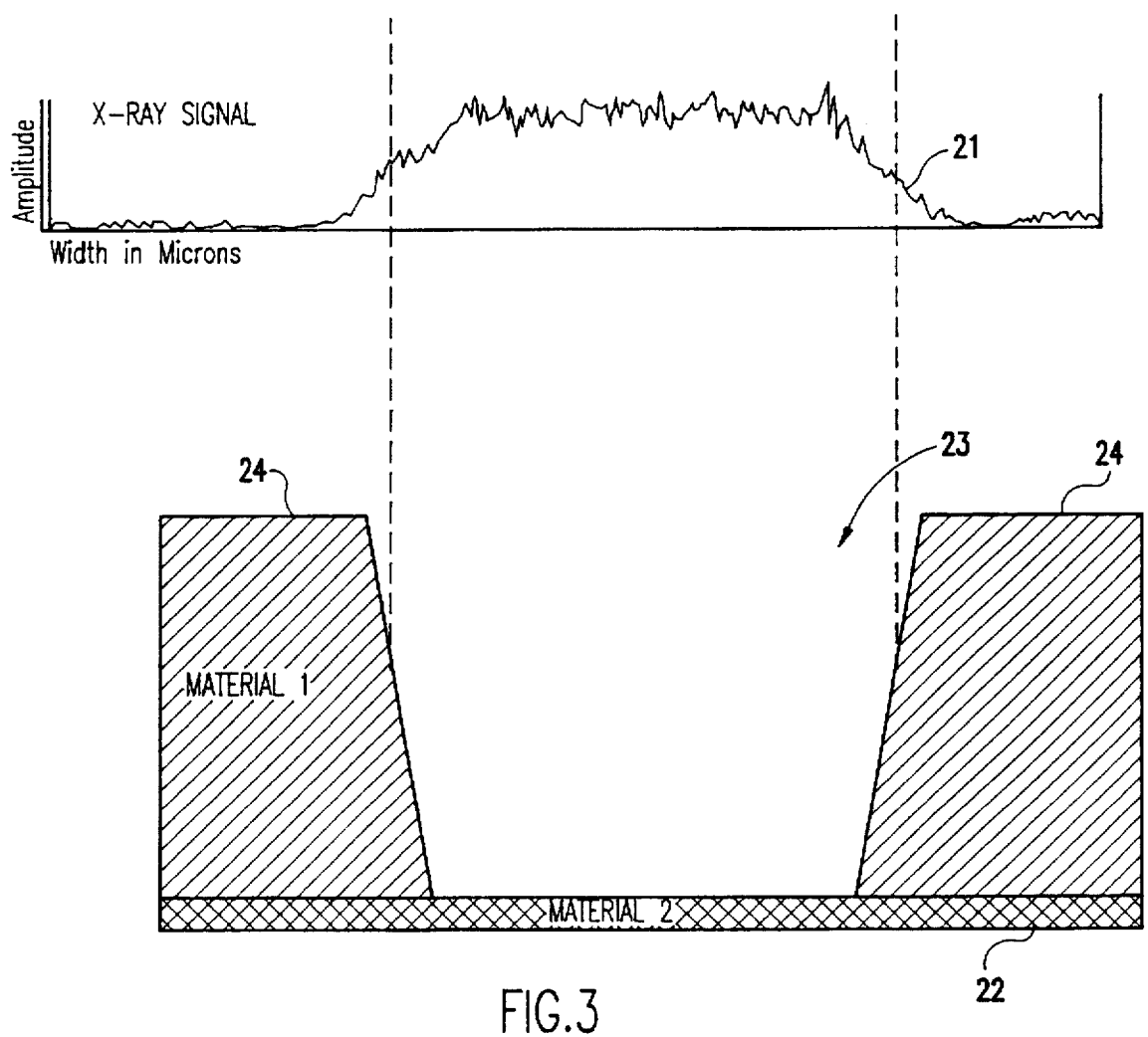
FIG. 3 is schematic drawing illustrating an X-ray signal matched to a cross section of a structure having a trench.

The primary SEM beam is scanned across the feature while the X-ray emission in the material of interest is measured in an energy band containing the flourescent X-ray peak chosen for the measurement. Primary beam electrons that collide directly with the material of interest cause flourescent X-rays to be emitted. Primary beam electrons colliding directly with other materials are both down-scattered in energy and spatially dispersed and thus will not cause the creation of significant number of flourescent X-rays in the peak region of interest. Thus, high X-ray signal contrast can be achieved for the material of interest. The intensity of the X-ray signal is recorded versus the position of the primary SEM beam. FIG. 3 illustrates the relationship. FIG. 3 matches an X-ray signal 21 with a cross section of a wafer 22 having a trench 23 structure surrounded by a resist 24 material. As can be seen the signal 21 is strongest where it is matched with the base of the trench 23. Where the SEM beam would have scanned resist 24 the signal 21 does not show similar peaks. Thus, the signal 21 can be measured to provide a measurement of the base of the trench 23.

Figure 4:
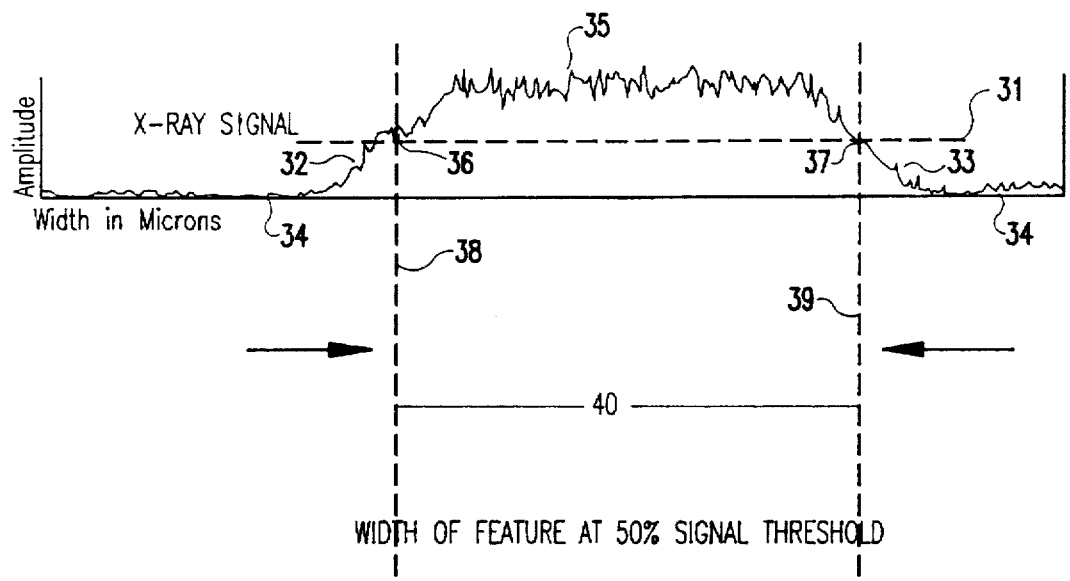
FIG. 4 is a graph of an X-ray signal.

Feature width is determined by inspection of the X-ray signal versus the known position of the SEM beam using a suitable measurement algorithm. In this case, because of the high signal contrast, simple thresholding techniques are adequate to determine line width although more sophisticated methods involving signal filtration and interpolation are recommended. FIG. 4 illustrates how the feature width can be determined via thresholding of the X-ray signal. In FIG. 4 the feature width is measured by measuring the length of the signal produced by the feature. Here, a horizontal line 31 is drawn across the where the signal has reached 50% of maximum. The signal has an increasing incline 32 when the feature is first detecting and a decreasing incline 33 when the scan over the feature is complete. Increasing and decreasing lines are achieved by fitting a line to the observed signal by a mathematical method such as a least squares fit. In this particular scan the width of the beam is actually a length equal to the distance between the flat area where no detection is found 34 and the raised flat signal 35 after the feature is detected. Knowing the width of the beam, one can determine that feature is present between points 36 and 37 where horizontal line 31 crosses increasing incline 32 and decreasing incline 33. Vertical lines 38 and 39 are drawn through points 36 and 37 to represent the bounds of the feature. The measured distance 40 between vertical line 38 and 39 provides the width of the feature detected by the scan. Determining where to choose points to be measured is dependent on the size and shape of the beam used.

Figure 5:
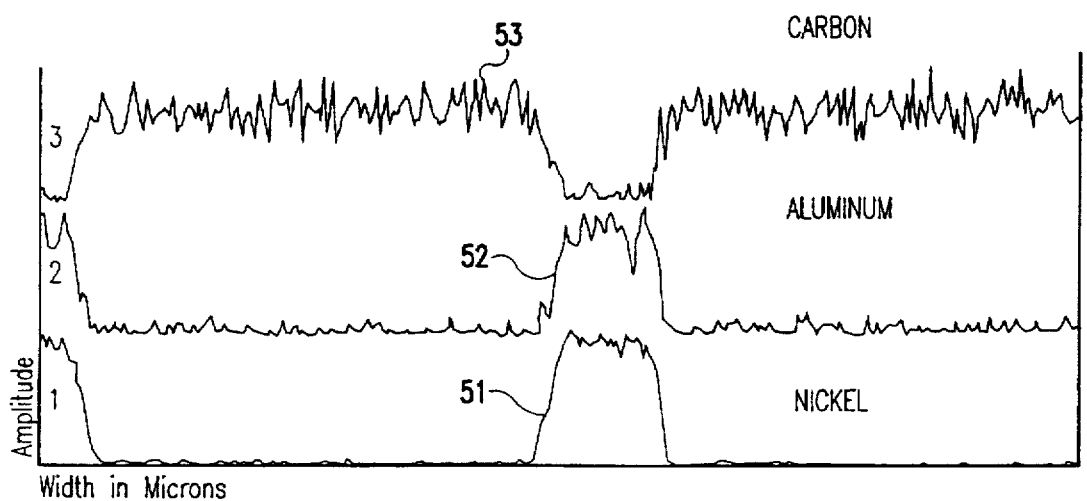
FIG. 5 is a graph showing carbon, aluminum and nickel X-ray signals.

FIG. 5 shows the results of three different scans of a substrate having a resist layer. The resist contains carbon and has a trench which is etched to a base containing nickel and aluminum. These scans show how a trench or other structure may be detected either by detecting substance in the substrate or in the structure. The scans for nickel 51 and aluminum 52 show similar results in which a steady group of peaks is recorded at the point where the trench was scanned. These groupings may be measured to determine the width of the base of the trench. The scan for carbon 53 reveals peaking all around the trench. These results may also be measured to determined the width of the trench.

The measurement was specifically created for the measurement of critical dimensions of a write pole tip track width measurement of a magneto-resistive (MR) head. It is a critical measurement that is essential to current and future generations of thin film disk head products. In addition, it is clear that this technique also applies to future semiconductor products. Specifically, the technique is applicable to sub-micron via holes and line features typical of complementary metal oxide semiconductor (CMOS) structures, such as sub-micron memory devices. The measurement technique according to the invention is generic and useful in the production of semiconductors, thin film recording heads and micro machined devices. As device dimensions shrink below 0.7 micron, optical techniques become impractical. Current SEM techniques experience contrast problems below 0.25 micron. AFM technology is not universally applicable and has performance difficulties in the manufacturing environment.

The method has been demonstrated using a Phillips scanning electron beam microscope fitted with a Tracor energy dispersive X-ray spectrometer containing a nitrogen cooled silicon detector on a product sample containing a write pole tip structure consisting of a 4 micron rectangular trench in photo resist on top of a planar nickel-iron seed layer. The magnitude (in counts per minute) of flourescent X-rays in the peak region was recorded for nickel and carbon as a 500 nm wide 6 Kev primary electron beam was scanned across the feature. The position of the primary electron beam was simultaneously recorded. The results (shown in FIG. 2) clearly demonstrate both the high signal contrast and feature width consistent with the known feature dimensions. In addition the results demonstrate the practicality of the measurement. Some key aspects of a practical embodiment include:

1. Positioning the detector directly in the SEM chamber without intervening material between the sample and the detector surface to allow efficient detection of low Z materials.
2. Using thermo-electric (Peltier effect) devices to cool, warm and in general control the temperature of the detector.
3. Using multiple detectors to provide better information and tolerance of different sample geometries.
4. Placing the detector close to the point of beam impact on the sample to allow more efficient X-ray collection for better signal to noise and/or shorter measurement times.

While the invention has been described in terms of a single preferred embodiment, those skilled in the art will recognize that the invention can be practiced with modification within the spirit and scope of the appended claims.

Having thus described our invention, what we claim as new and desire to secure by Letters Patent is as follows:

1. A method of measuring the lateral dimension of a structure where said structure is composed of at least two atomically different materials comprising the steps of:

scanning an electron beam across a feature to be measured, said electron having a primary beam energy sufficient to excite flourescent X-rays characteristic of one of the at least two atomically different materials and having a lateral beam dimension that is sufficiently small compared to the lateral dimension of the feature being measured;

detecting, counting and recording a counted number of characteristic X-rays so produced against a known position of the electron beam; and analyzing the recorded X-ray counts versus beam position to determine the width dimension of the feature.

2. The method recited in claim 1 wherein said electron beam is produced in a scanning electron microscope.

3. The method recited in claim 1 wherein said characteristic X-rays are detected using an energy dispersive X-ray detection system.

4. The method recited in claim 1 wherein said recorded X-ray counts versus beam position is analyzed using a threshold method in which the lateral dimension of the feature is determined as the spatial extent of said recorded X-ray counts which exceed a given number.

5. The method recited in claim 1 wherein the electron beam's primary electron energy is set at or above the energy of an X-ray flourescence peak characteristic of said one material.

6. The method recited in claim 5 wherein the characteristic X-rays are detected in an energy band containing the X-ray flourescence peak.

* * * * *